(12) United States Patent  
Brouwer et al.

(10) Patent No.: US 8,064,038 B2  
(45) Date of Patent: Nov. 22, 2011

(54) INSPECTION APPARATUS, LITHOGRAPHIC SYSTEM PROVIDED WITH THE INSPECTION APPARATUS AND A METHOD FOR INSPECTING A SAMPLE

(75) Inventors: Egbert Anne Martijn Brouwer, Zoetermeer (NL); Hedser Van Brug, 's-Gravenhage (NL)

(73) Assignee: ASML Netherlands B.V., Veldhoven (NL)

( * ) Notice: Subject to any disclaimer, the term of this patent is extended or adjusted under 35 U.S.C. 154(b) by 625 days.

(21) Appl. No.: 11/607,097

(22) Filed: Dec. 1, 2006

(65) Prior Publication Data

US 2007/0146695 A1    Jun. 28, 2007

Related U.S. Application Data

(63) Continuation-in-part of application No. 11/317,243, filed on Dec. 27, 2005, now Pat. No. 7,522,263.

(51) Int. Cl.  
*G03B 27/42* (2006.01)  
*G03B 27/52* (2006.01)

(52) U.S. Cl. .................................... 355/53; 355/30

(58) Field of Classification Search .......... 355/53, 355/30, 67, 72, 75; 356/237.5  
See application file for complete search history.

(56) References Cited

U.S. PATENT DOCUMENTS

| | | |
|---|---|---|
| 4,837,447 A | 6/1989 | Pierce et al. |
| 5,416,594 A | 5/1995 | Gross et al. |
| 5,559,584 A | 9/1996 | Miyaji et al. |
| 5,853,962 A | 12/1998 | Bowers ........................ 430/331 |
| 5,917,590 A | 6/1999 | Greve ........................ 356/237.3 |
| 5,936,734 A | 8/1999 | Johs et al. ..................... 356/364 |
| 6,038,015 A | 3/2000 | Kawata .......................... 355/67 |
| 6,055,742 A | 5/2000 | Kim |
| 6,288,769 B1 | 9/2001 | Akagawa et al. |
| 6,305,097 B1 | 10/2001 | Salamati-Saradh et al. |
| 6,327,021 B1 | 12/2001 | Higashiguchi |
| 6,392,738 B1 | 5/2002 | Van De Pasch ................. 355/30 |
| 6,394,109 B1 | 5/2002 | Somekh |
| 6,395,102 B1 | 5/2002 | Salamati-Saradh et al. |
| 6,589,354 B2 | 7/2003 | Reid |
| 6,621,568 B1 | 9/2003 | Yonezawa |
| 6,671,051 B1 | 12/2003 | Nikoonahad ................. 356/445 |

(Continued)

FOREIGN PATENT DOCUMENTS

JP    55-15620    2/1980

(Continued)

OTHER PUBLICATIONS

First Non-Final Office Action mailed Jun. 29, 2007 for U.S. Appl. No. 11/318,055, filed Dec. 27, 2005, 8 pgs.

(Continued)

*Primary Examiner* — Peter B Kim  
(74) *Attorney, Agent, or Firm* — Sterne, Kessler, Goldstein & Fox P.L.L.C.

(57) ABSTRACT

The invention relates to an inspection apparatus and a method for inspecting a sample, such as a lithographic patterning device or mask, for anomalies, such as contamination particles or defects. The inspection apparatus includes a support structure constructed and arranged to support the sample, and a radiation system constructed and arranged to radiate a sample with a radiation beam. The radiation system is provided with a first polarizer. The apparatus also includes a detection system constructed and arranged to detect radiation that is reflected from the sample with a detector. The detection system is provided with a second polarizer.

31 Claims, 8 Drawing Sheets

U.S. PATENT DOCUMENTS

| | | | |
|---|---|---|---|
| 6,694,284 B1 | 2/2004 | Nikoonahad et al. | 702/155 |
| 2002/0057425 A1 | 5/2002 | Nakano | |
| 2002/0094685 A1 | 7/2002 | Nakata et al. | |
| 2003/0045098 A1 | 3/2003 | Verhaverbeke et al. | |
| 2003/0058424 A1 | 3/2003 | Ramamoorthy et al. | |
| 2003/0218728 A1 | 11/2003 | del Puerto et al. | |
| 2004/0125375 A1 | 7/2004 | Some | 356/369 |
| 2004/0140298 A1 | 7/2004 | Widmann et al. | |
| 2004/0150820 A1 | 8/2004 | Nikoonahad | 356/364 |
| 2004/0180270 A1 | 9/2004 | Heerens | |
| 2004/0185682 A1 | 9/2004 | Foulke et al. | |
| 2004/0233442 A1 | 11/2004 | Mieher | 356/401 |
| 2004/0256613 A1 | 12/2004 | Oda et al. | |
| 2005/0016679 A1 | 1/2005 | Ruzic | 156/345.5 |
| 2005/0030505 A1 | 2/2005 | Miwa | |
| 2005/0058836 A1 | 3/2005 | Goldstein | 428/411.1 |
| 2005/0206887 A1* | 9/2005 | Morioka et al. | 356/237.5 |
| 2005/0275816 A1* | 12/2005 | Lee | 355/30 |
| 2006/0066854 A1 | 3/2006 | Meeks | 356/369 |
| 2006/0082743 A1 | 4/2006 | Yonekawa et al. | |
| 2006/0176460 A1 | 8/2006 | Phillips et al. | |
| 2007/0146657 A1 | 6/2007 | Mierlo et al. | |
| 2007/0146658 A1 | 6/2007 | Van Mierlo et al. | |

FOREIGN PATENT DOCUMENTS

| | | |
|---|---|---|
| JP | 58-21742 A | 2/1983 |
| JP | 61-10237 A | 1/1986 |
| JP | 61-159730 | 7/1986 |
| JP | 61-207953 | 9/1986 |
| JP | 62-62251 | 3/1987 |
| JP | 63-41855 | 2/1988 |
| JP | 3-155550 A | 7/1991 |
| JP | 6-283488 | 10/1994 |
| JP | 7-169663 | 7/1995 |
| JP | 8-78182 A | 3/1996 |
| JP | 8-124822 A | 9/1996 |
| JP | 8-321480 | 12/1996 |
| JP | 11-101742 | 4/1999 |
| JP | 2000-58494 | 2/2000 |
| JP | 2001-358046 | 12/2001 |
| JP | 2003-022993 | 1/2003 |
| JP | 2004-141704 | 5/2004 |
| JP | 2004-152843 | 5/2004 |
| KR | 2001-0066292 A | 7/2001 |
| KR | 2001-0083591 A | 9/2001 |
| RU | 2149425 | 5/2000 |
| WO | WO 2004/076963 A2 | 9/2004 |
| WO | WO 2004/095136 A2 | 11/2004 |
| WO | WO 2005/108914 A2 | 11/2005 |

OTHER PUBLICATIONS

Final Rejection mailed Dec. 28, 2007 for U.S. Appl. No. 11/318,055, filed Dec. 27, 2005, 11 pgs.
Second Non-Final Office Action mailed Jun. 11, 2008 for U.S. Appl. No. 11/318,055, filed Dec. 27, 2005, 9 pgs.
Third Non-Final Office Action mailed Dec. 17, 2008 for U.S. Appl. No. 11/318,055, filed Dec. 27, 2005, 9 pgs.
Official Action issued for Japanese Patent Application No. JP 2003-321110 dated Jan. 20, 2006.
International Search Report issued for PCT Patent Application No. PCT/NL2006/000605 dated Apr. 17, 2007.
Meiling et al., "The EUV Project at ASML: an update," Emerging Lithographic Technologies VII, Proceedings of SPIE, vol. 5037 (2003), pp. 24-35.
Non-Final Rejection mailed Jun. 12, 2009 for U.S. Appl. No. 11/318,055, filed Dec. 27, 2005, 8 pgs.
Postava et al., "Null Ellipsometer with Phase Modulation", Optics Express, vol. 12, No. 24, Nov. 29, 2004, pp. 6040-6045.
English Abstract of JP 58-21742 published Feb. 8, 1983, 2 pgs.
English Abstract of JP 61-10237 published Jan. 17, 1986, 1 pg.
English Abstract of JP 3-155550 published Jul. 3, 1991, 2 pgs.
English Abstract of JP 8-78182 published Mar. 22, 1996, 2 pgs.
English Abstract of JP 8-124822 published May 17, 1996, 2 pgs.

* cited by examiner

INSPECTION APPARATUS, LITHOGRAPHIC SYSTEM PROVIDED WITH THE INSPECTION APPARATUS AND A METHOD FOR INSPECTING A SAMPLE

CROSS-REFERENCE TO RELATED APPLICATIONS

This application is a continuation-in-part of U.S. patent application Ser. No. 11/317,243, which was filed on Dec. 27, 2005 (now U.S. Pat. No. 7,522,263 B2, issued Apr. 21, 2009), the entire content of which is hereby incorporated by reference in its entirety.

FIELD

The present invention relates to an inspection apparatus for inspecting a sample for anomalies, a lithographic apparatus that is provided with such an inspection apparatus, and a method for inspecting a sample.

BACKGROUND

A lithographic system applies a desired pattern onto a substrate, usually onto a target portion of the substrate. A lithographic system can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive compound (resist) provided on the substrate. In general, a single substrate will contain a network of adjacent target portions that are successively patterned.

Being able to guarantee defect-free imaging in extreme ultraviolet light (EUV) lithographic systems may be necessary for a successful introduction and acceptance in the market of EUV lithographic systems. Particles on the patterning device are one of the main sources of imaging defects, because the EUV patterning device is not covered by a membrane or pellicle (as is common for deep ultraviolet light (DUV) patterning devices) which keeps any contamination out of focus. For the next generation lithography tools, particles with a diameter of 30 nm and larger may be detrimental. Inspecting the patterning device before moving the patterning device to an exposure position is a desired aspect of a patterning device handling process for extreme ultraviolet patterning devices.

SUMMARY

It is desirable to provide an inspection apparatus for inspecting a sample for anomalies. The sample may, for example, be (a part of) a patterning device or a substrate, and the anomalies may be a particle or a defect.

According to an embodiment of the invention, there is provided an inspection apparatus for inspecting a sample for anomalies. The apparatus includes a support structure constructed and arranged to support the sample, and a radiation system constructed and arranged to radiate the sample with a radiation beam. The radiation system is provided with a first polarizer. The apparatus also includes a detection system constructed and arranged to detect a detection beam with radiation that is reflected from the sample with a detector. The detection system is provided with a second polarizer. The sample may be a patterning device, and the anomalies may be particles or defects in the patterned structure on the sample.

The invention further relates to a lithographic system that includes a patterning device support constructed and arranged to support a patterning device. The patterning device is capable of imparting a radiation beam with a pattern in its cross-section to form a patterned radiation beam. The apparatus also includes a substrate table constructed and arranged to hold a substrate, a projection system constructed and arranged to project the patterned radiation beam onto a target portion of the substrate, and an inspection apparatus constructed and arranged to inspect the patterning device. The inspection apparatus includes a radiation system constructed and arranged to radiate the patterning device with a second radiation beam. The radiation system is provided with a first polarizer. The inspection apparatus also includes a detection system constructed and arranged to detect a detection beam with radiation that is reflected from the patterning device with a detector. The detection system is provided with a second polarizer.

The invention further relates to a method for inspecting a sample for anomalies. The method includes directing a radiation beam with a polarization produced by a first polarizer to the sample with a radiation system, and receiving a reflected detection beam from the sample via a second polarizer on a detector provided to a detection system.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1A:
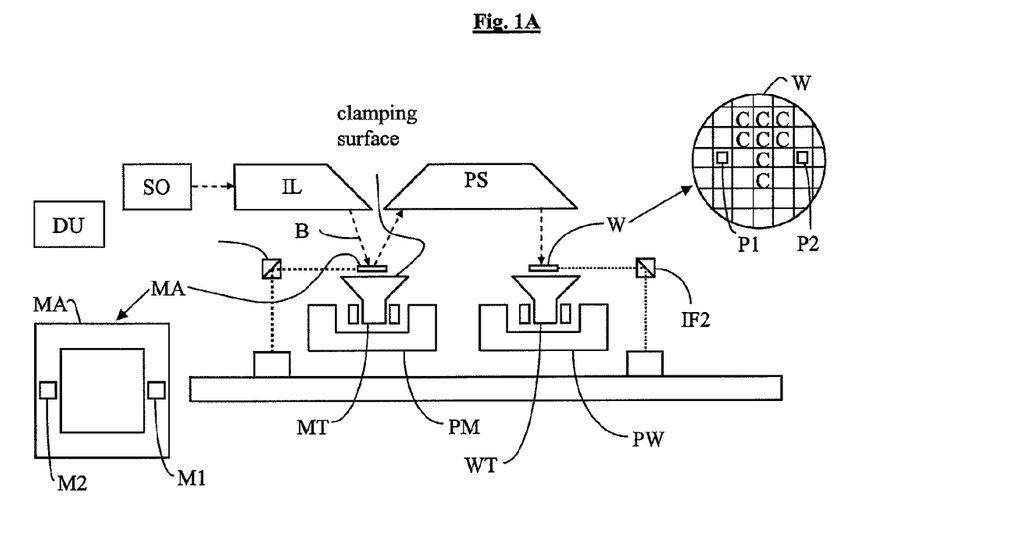
FIG. 1A depicts a lithographic system provided with an inspection apparatus according to an embodiment of the invention.

FIG. 1A schematically depicts a lithographic system according to one embodiment of the invention. The apparatus comprises: an illumination system (illuminator) IL configured to condition a radiation beam B (e.g. UV radiation or EUV radiation); a patterning device support (e.g. a mask table) MT constructed to support a patterning device (e.g. a mask) MA and connected to a first positioner PM configured to accurately position the patterning device in accordance with certain parameters; a substrate table (e.g. a wafer table) WT constructed to support a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support supports, i.e. bears the weight of, the patterning device. It holds the patterning device in a manner that depends on the orientation of the patterning device, the design of the lithographic system, and other conditions, such as, for example, whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example, with respect to the projection system. Any use of the terms "reticle" or "mask" herein may be considered synonymous with the more general term "patterning device."

The term "patterning device" as used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" as used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a reflective type (e.g. employing a reflective mask). Alternatively, the apparatus may be of a transmissive type (e.g. employing a transmissive mask).

The lithographic system may be of a type having two (dual stage) or more substrate tables (and/or two or more mask tables). In such "multiple stage" machines, the additional tables may be used in parallel, or preparatory steps may be carried out on one or more tables while one or more other tables are being used for exposure.

The lithographic system may also be of a type wherein at least a portion of the substrate may be covered by a liquid having a relatively high refractive index, e.g. water, so as to fill a space between the projection system and the substrate. An immersion liquid may also be applied to other spaces in the lithographic system, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic system may be separate entities, for example when the source is an excimer laser. In such cases, the source is not considered to form part of the lithographic system and the radiation beam is passed from the source SO to the illuminator IL with the aid of a beam delivery system comprising, for example, suitable directing mirrors and/or a beam expander. In other cases the source may be an integral part of the lithographic system, for example when the source is a mercury lamp. The source SO and the illuminator IL, together with the beam delivery system if required, may be referred to as a radiation system.

The illuminator IL may comprise an adjuster for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator and a condenser. The illuminator may be used to condition the radiation beam, to have a desired uniformity and intensity distribution in its cross-section.

The radiation beam B is incident on the patterning device (e.g., mask MA), which is held on the patterning device support (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF2 (e.g. an interferometric device, linear encoder or capacitive sensor), the substrate table WT can be moved accurately, e.g. so as to position different target portions C in the path of the radiation beam B. Similarly, the first positioner PM and another position sensor IF1 can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes a programmable patterning device, such as a programmable mirror array of a type as referred to above.

At present, particle contamination of patterning devices MA has limited influence of the patterns applied to substrates W. Due to the wavelength of radiation used to pattern the substrates W, small particle contamination of the patterning device MA has little effect on the propagation and patterning of the radiation beam B. Present patterning devices (e.g. reticles) typically use a protective pellicle that is spaced away from the patterning device MA. Any contamination will be deposited on the protective pellicle, and will not form part of the pattern imaged onto the substrate W by the projection system PS. However, with the ongoing development of lithographic systems, the wavelengths used to pattern substrates W are decreasing. Many proposed lithographic systems will use EUV radiation (e.g. having a wavelength in the range of 5-20 nm), but a protective pellicle can no longer be used, as it will absorb the EUV radiation. It will be appreciated that contamination of the patterning device MA can lead to defects in the patterns applied to the substrate W, and therefore lead to a reduction in the yield of acceptably patterned substrates W.

There are many occasions during the life of a patterning device in which particle contamination can occur. For example, if the cleaning of the patterning device MA is undertaken in a separate facility, independent of the lithographic system, the patterning device may become contaminated after its cleaning during moving it to the lithographic system and loading it onto the patterning device support MT in the lithographic system. At present, there is no inspection or cleaning of the patterning device MA immediately before loading of the patterning device MA into the lithographic system, or within the apparatus itself. It is only after exposure of the substrate W that defects due to particle contamination are detected in the pattern applied to the substrate W. By this time, the substrate W has already been exposed, and contains a defective pattern. In many circumstances, part of the substrate W is now useless (or may need lengthy repair processes to be reusable), which is costly and reduces the yield.

By providing a cleaning unit that is arranged to clean the patterning device MA in-situ, the problem of contaminating the patterning device between initial cleaning at a separate facility and loading it onto the patterning device support MT is reduced and/or avoided.

Figure 1B:
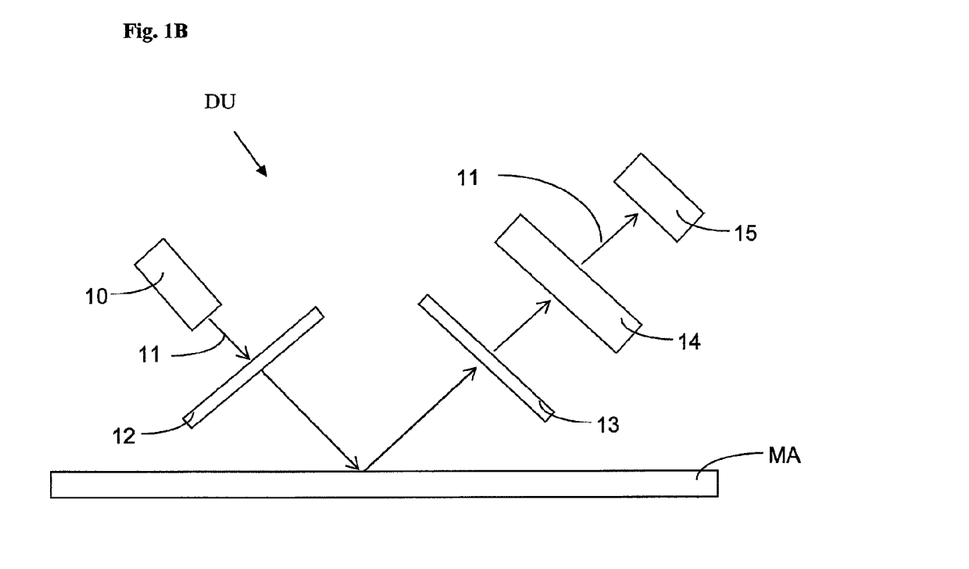
FIG. 1B depicts the inspection apparatus of FIG. 1A according to an embodiment of the invention.

FIG. 1A shows a lithographic system with an inspection apparatus DU arranged to detect contamination of the patterning device MA in-situ (i.e. within or in communication with the lithographic system). The inspection apparatus may also be located within a vacuum space within the lithographic system or may be located such that the sample may be in the vacuum space, while most of the hardware of the inspection apparatus is kept out of the vacuum space. With most hardware of the inspection apparatus being kept out of the vacuum, the hardware does not need to be vacuum compatible which facilitates easy design. FIG. 1B illustrates a first embodiment of the invention. The first embodiment is depicted as a separate unit but it may optionally also be provided as an in-situ unit as described with reference to FIG. 1A. As a separate unit, it may be used for inspection purposes of a patterning device (e.g. mask). As an in-tool unit, it may perform a quick inspection of the patterning device MA prior to a lithographic process.

An embodiment of the inspection apparatus DU is shown in detail in FIG. 1B, which illustrates an ellipsometric apparatus performing an ellipsometric analysis for inspecting of the sample (e.g. patterning device) MA for anomalies (e.g. contamination particles). The apparatus comprises a radiation system provided with a source 10, and the radiation system is constructed and arranged to direct a radiation beam 11 towards a part of the surface of the patterning device MA where detection of particle contaminants is desired. The patterning device MA may be supported by a support structure, such as the patterning device support MT discussed above. The radiation beam 11 is polarized by a first polarizer 12 provided to the radiation system before the radiation beam 11 is incident on the patterning device MA.

The first polarizer 12 may be a linear polarizer that allows only light with a certain polarization to pass. The light in the beam is then linearly polarized. By rotating the first polarizer 12 with a rotator RO, linearly polarized light with the direction of polarization corresponding to the direction of rotation may be produced from randomly polarized light. If linearly polarized light of a known orientation is reflected at oblique incidence from a surface, the reflected light in general will be elliptically polarized. The reflected and now elliptically polarized detection beam 11 passes through a quarter wave plate 13 and an analyzer 14 before being detected by the detector 15. The quarter wave plate 13, the analyzer 14 and the detector 15 are provided to a detection system DU. The analyzer 14 comprises a second polarizer 14 that may be rotated by a rotator. The quarter wave plate 13 may also be rotated by a rotator RO and may alternatively be provided between the radiation source 10 and the patterning device or may be completely left out of the inspection apparatus DU. The quarter wave plate 13 functions as a retarder (or compensator) and, depending on its orientation, may transform the ellipse of polarization, e.g. linearly polarized light into circularly polarized light when set to 45.degree. with respect to the linear polarization axis. The polarization of the reflected light 11 may be adjusted using the quarter wave plate 13, the first polarizer 12 or the second polarizer 14 by varying their respective rotational orientations until no light passes through the second polarizer (i.e. until no light is detected by the detector). From the rotational orientations of the quarter wave plate 13 and the first and second polarizers 12, 14, when no light is detected, the amplitude and phase change of the polarization introduced by reflection from the surface of the patterning device MA can be calculated. From the polarization change, the size (or thickness) of contamination of the patterning device MA may be calculated. The detector 15 may be a camera and a magnifying optical projection system or microscope objective may be positioned between the patterning device and the detector so that an image may be made of the inspection field. An ellipsometer with a camera may be called an imaging ellipsometer. The magnifying optical projection system or microscope objective with a long working distance may have a magnification of between 10 and 100 times and the inspection field may be something of 1 mm$^2$. The particle inspection apparatus may be constructed and arranged to radiate the radiation beam to the patterning device with an angle with respect to the normal of the surface of the patterning device and to inspect the detection beam that is reflected from the patterning device at the same angle from the normal.

When linearly polarized light is incident on a patterning device, the reflected light will in general exhibit an elliptical state of polarization, and the same elliptical state of polarization (but with a reversed state of rotation) incident on the patterning device will generate a linearly polarized reflection. By finding the rotation of the linear polarized reflection and by extinguishing it by rotating the second polarizer and the retarder so that no signal gets through, one can find the "null" position. Any deviation from the null position caused by, for example, a contaminant particle on the patterning device will create a bright spot on the null dark image, which makes the nulling imaging ellipsometer very sensitive for detection of particles. In an embodiment, the detected particles are smaller than about 200 nm in size.

Alternatively, the inspection apparatus can be provided with a modulation system to provide a small modulation to the radiation beam or the detection beam by modulating the first or second polarizer or the retarder. One of the first and second polarizer or the retarder can rotate continuously to provide a modulation to the radiation or detection beam so that a periodic (e.g. sine shaped) signal will be detected by the detector. The apparatus may be provided with a control system to control this continuous rotation and/or the modulation. A small phase modulation may be applied to the radiation or detection beam, according to Postava et al., Optics Express, Vol. 12 (2004), pp. 6040-6045, for example.

The inspection apparatus may be provided with a control system CS connected with the detector 15 and connected with the rotator RO for rotating one or more of the first and second polarizers or the retarder. The control system CS may be used to find a position of the first and second polarizer, and the retarder in which substantially no signal ($10^{-8}$ compared to normal intensity) is measured from the patterned structure on the patterning device MA. In that position, any signal (in the dark) on the detector 15 would mean a contamination particle. Detectors are rather sensitive if they have to look to a bright spot against a dark background. The particle inspection apparatus can be used in nulling ellipsometry with the control system automatically finding the nulling position or a position very close to it.

It will be appreciated that the above embodiments have been described by way of example only, and that various modifications can be made thereto. It will be appreciated that the inspection apparatus DU (or a part thereof) may be moved to detect contamination of a particular part of the patterning device MA. Conversely, the patterning device MA may be moved toward and relative to the particle inspection apparatus DU. It may be necessary to scan the surface (or surfaces) of the patterning device MA to detect particle contaminants thereon. In this case, it may be suitable to scan the particle inspection apparatus DU relative to the patterning device MA, or conversely, scan the patterning device MA relative to the particle inspection apparatus DU.

The particle inspection apparatus DU may comprise optics for directing light with a wavelength between 150 and 2000 nm to the patterning device. The radiation system may be constructed and arranged to radiate light with a wavelength that is larger than the size of a patterned structure on the patterning device. This may have the advantage that the structures on the patterning device may not influence the measurement of the detector and the signal on the detector may then be purely determined by contaminant particles on the patterning device.

In an embodiment, the inspection apparatus DU may be an imaging ellipsometer. The above-described detector 15 may then be a camera with, for example, a microscope objective with a long working distance as the magnifying optics projection system so that a two dimensional field may be imaged in one time on, for example, a CCD array. The field that can be imaged in one time may be 1 mm$^2$ with a resolution of 1 μm which will make it possible to scan a whole patterning means in a relatively short time and to detect small particles at the same time.

Although in some instances it may only be necessary to determine whether one surface of the patterning device MA is contaminated, it will often be the case that it is necessary to determine whether either surface of the patterning device is contaminated or damaged. For this purpose, the particle inspection apparatus DU may be provided with a rotating unit for rotating the patterning device MA such that first the patterned structures on the patterning device can be inspected, and second the clamping surface of the patterning device MA can be detected, or the other way around. The particle inspection apparatus may also be constructed and arranged that both the patterned surface and clamping surface may be detected without rotating the patterning device MA.

The particle inspection apparatus DU may be of any suitable configuration and/or orientation and may be positioned at an angle with respect to the patterning device MA. When detecting particle contamination on the surface (or surfaces) of the patterning device MA, the patterning device MA may be rotated such that the surface which imparts a pattern to the cross section of the radiation beam B is facing downwards when detection takes place. The patterning device MA is rotated to face downwards to reduce the possibility of additional particle contaminants falling onto the patterning side of the patterning device MA. However, it may be preferable to avoid rotation of the patterning device where possible, for example to save space or time (or even to simplify equipment used to control movement of the patterning device MA). Various techniques may be used where the properties of a first surface can be derived from the (e.g. optical) properties of a second, opposite surface.

The particle inspection apparatus DU described above has been described as detecting particle contaminants on the patterning device in-situ. In-situ has been described as a location substantially within the lithographic system, or in communication therewith, such that detection of particle contaminants on the patterning device may be undertaken without having to transport the patterning device outside the lithographic system or even to transport it outside the vacuum within the lithographic system. This is useful for EUV lithography, since a very high vacuum is required with an EUV lithography apparatus. It may also be useful for lithography apparatus which use other wavelengths. Detection of particle contaminants on the patterning device may be undertaken without having to transport the patterning device to a separate detection facility, remote from the lithographic system, reducing the possibility of contaminating the patterning device during transport.

Figure 1C:
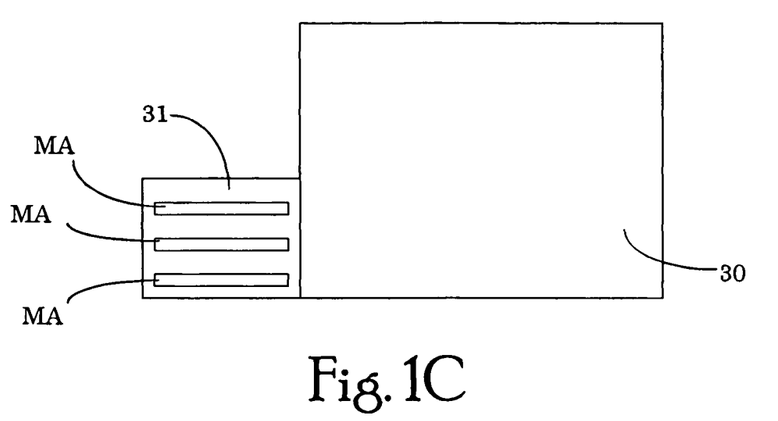
FIG. 1C depicts a simplified lithographic system in accordance with an embodiment of the present invention.

FIG. 1C illustrates a schematic view of a lithographic system in accordance with an embodiment of the present invention. The lithographic system has been shown in an extremely simplified format to aid the explanation of the term 'in-situ' used herein. The lithographic system comprises a first chamber 30 (e.g. an evacuated or vacuum chamber), where exposure of the substrates W takes place, and a second or transfer chamber 31 in communication with the evacuated chamber 30. The second chamber 31 is used to introduce masks to the evacuated chamber 30, and to remove masks from the evacuated chamber 30. For example, different or replacement masks MA may be located in the second chamber 31 for introduction into the evacuated chamber 30. A robot chamber (not shown) may, for example, form part of the first chamber 30, and may be arranged to handle masks received from the second chamber 31. The robot chamber may be provided with a gripping device to grip and handle the objects.

Figure 1D:
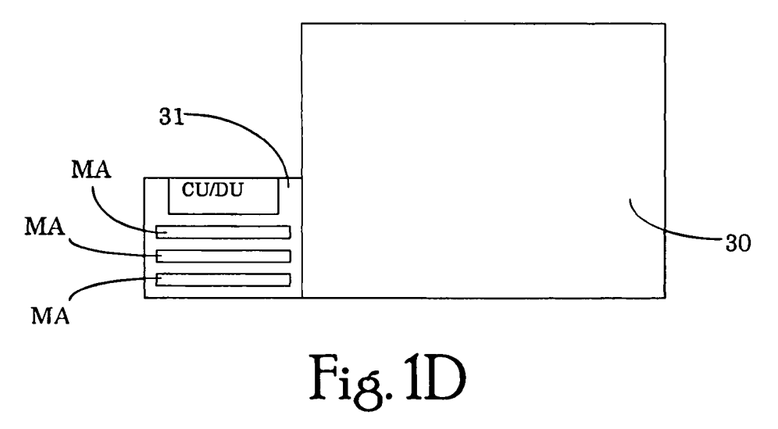
FIG. 1D depicts a simplified lithographic system in accordance with an embodiment of the present invention.

FIG. 1D shows a cleaning unit CU and/or particle inspection apparatus DU located in the second chamber 31 (e.g. mask MA storage chamber 31). By locating the cleaning unit CU and/or particle inspection apparatus DU in the mask MA storage chamber 31, the substrates W may be cleaned and/or scanned for contamination in-situ. The lithographic system is self-contained, such that when detection or cleaning has taken place in the mask MA storage chamber 31, no more (or at least, very little) contamination can be added to the surface of the mask MA when it is introduced from the mask storage chamber 31 into the evacuated chamber 30. Indeed, the mask storage chamber 31 is often evacuated, sometimes to the same extent as the evacuated chamber 30 to reduce contamination. In an embodiment, a door may be provided between the mask storage chamber 31 and the evacuated chamber. The door may be closed, following which cleaning of a mask may take place. Any gas which passes into the mask storage chamber 31 may be pumped out, to restore the vacuum, before the door is opened. Therefore, the mask MA can be cleaned without destroying the vacuum in the evacuated chamber. Since the mask storage chamber 31 forms part of the lithographic system, cleaning of the mask MA takes place in-situ in the lithographic system.

Figure 1E:
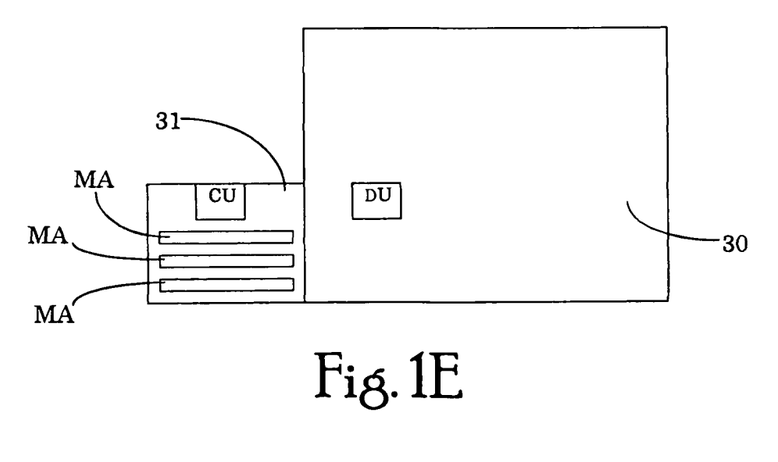
FIG. 1E depicts a simplified lithographic system in accordance with an embodiment of the present invention.

FIG. 1E illustrates a modification of the lithographic system of FIG. 1D. Specifically, the cleaning unit CU is now located in the patterning device MA storage chamber 31, whereas the particle inspection apparatus DU is located in the evacuated chamber 30. It will be appreciated that the cleaning unit CU and particle inspection apparatus DU may be located in any suitable location within the lithographic system. In some circumstances however, it may be desirable to locate the cleaning unit away from the evacuated chamber 30, so that any particle contaminants removed from the surface of the patterning device MA by, for example, exposure to high pressure carbon dioxide are not deposited on other sensitive surfaces of the lithographic system within the evacuated chamber 30.

Whereas the cleaning unit CU and particle inspection apparatus DU have been described as being located within an evacuated vacuum chamber 30 or a second vacuum chamber 31 in communication therewith, the cleaning unit CU and particle inspection apparatus DU may be placed in any suitable location. An advantage of having the cleaning unit and particle inspection apparatus within the vacuum chambers may be that patterning devices MA only may be transported outside vacuum within a contamination protection box. Cleaning and detection of contamination may not be possible when the patterning device MA is within the box. A cleaning unit CU and/or particle inspection apparatus DU outside the vacuum system may need therefore a system for opening the box and removing the patterning device MA which imposes risks of contamination. The cleaning unit CU and/or particle inspection apparatus DU may be located anywhere where cleaning and detection may be undertaken in-situ (i.e. within or in communication with the lithographic system) so that, for example, a vacuum need not be destroyed for cleaning and/or detection to take place. For example, the cleaning unit CU and/or particle inspection apparatus DU may be located at one of a number of handling or stages of the patterning device MA (e.g. adjacent (which includes in or on) a handling or storage stage).

It will be appreciated that the lithographic system may comprise an inspection apparatus DU and/or a cleaning unit CU. The particle inspection apparatus DU and cleaning unit CU may be located in close proximity to each other, or at different parts of the lithographic system, far from one another. The particle inspection apparatus DU and cleaning unit CU may cooperate, such that the surface is scanned for contamination by the particle inspection apparatus DU, before it is cleaned (if necessary) by the cleaning unit CU. This process may be repeated until the patterning device MA is deemed clean enough to be used to pattern a substrate.

Although the present invention is applicable to all types of lithographic systems, it is particularly relevant to lithographic systems that use EUV radiation to apply a pattern to a substrate W. This is due to the fact that particle contamination is a particular problem of lithographic systems that employ such radiation to pattern a substrate, as described above.

Although the specific particle inspection apparatus and cleaning units described above in relation to FIGS. 1A-E have been referred to as being in-situ in the lithographic system, it will be appreciated that they may be provided at some other location.

It will be appreciated that in general in the above described embodiments, the patterning device MA is moved to a cleaning unit or particle inspection apparatus which is located away from the normal location of the pattern device in use. This may be expressed as saying that the patterning device is moved to a cleaning location or detection location. The cleaning location or detection location may comprise the patterning device storage chamber 31, or may comprise some other particular location within the lithographic system. The patterning device MA may be movable using a patterning device handler, examples of which are well known in the art. In some instances, the cleaning unit or the particle inspection apparatus may be movable.

The cleaning and particle inspection apparatus may also be constructed and arranged to clean or detect contamination on a clamping surface of the support structure MT or of the clamping surface of the substrate table WT. Contamination on the clamping surface of the support structure or the substrate table MT may also lead to deteriorated exposures from the mask MA on the substrate W.

An inspection apparatus for detecting particles may be based on elastic light scattering. For small particles ($\alpha \ll \lambda$), the scattered intensity is:

$$I \propto \left(\frac{1}{\lambda}\right)^4 \left(\frac{\varepsilon - \varepsilon_0}{\varepsilon + 2\varepsilon_0}\right)^2 a^6 \quad (1)$$

The first term on the right side is the dependence on the wavelength of the light; the second term is the dielectric contrast, which depends on the dielectric function of the particle $\in$ and the dielectric function of the surrounding medium $\in_0$. The particle diameter $\alpha$ enters this equation at the sixth power. Consequently, the reflected intensity drops when the particle size decreases. This may be disadvantageous for particle scanning applications.

Ellipsometry is a very sensitive optical technique for surface characterization. The physical principle behind ellipsometry is that the polarization of light changes when it is reflected at an interface between two optical media. Light reflecting at an interface can be decomposed in two components, parallel and perpendicular to the plane of incidence. In general both the ratio of these two components and their phase difference change. Both changes can be measured using an ellipsometer.

These changes are conventionally expressed in a single complex quantity:

$$\rho = \tan(\psi) \cdot \exp(i\Delta) \quad (2)$$

In this equation, $\tan(\psi)$ is the change in the ratio of the amplitudes and $\Delta$ is the phase change. Especially the phase difference can change significantly due to small changes at a surface, which is the cause of the high sensitivity of ellipsometry.

Several theories exist for description of the influence of small particles at surface on the ellipsometric parameters. The thin island film theory tends to give accurate results. Particles at the surface enter this theory as polarizabilities. The incident light polarizes the particles and this results in a change of the polarization of the reflected light. The polarizabilities depend in a favorable way on the particles' properties:

$$\gamma, \beta \propto \frac{\varepsilon - \varepsilon_0}{\varepsilon + 2\varepsilon_0} a^3 \quad (3)$$

The particle radius $\alpha$ only enters at the third power in this equation, which compares favorably with the sixth power in scattering and shows that ellipsometry may be an effective alternative for scattering in particle scanning applications.

An ellipsometer comprises a light source, a polarizer, a sample, a second polarizer (called the analyzer) and a detection system. Many ellipsometers also include a compensator before or after the sample. The compensator is used to shift the relative phase of the two polarization states. It can convert linear polarized light to elliptical polarized light and vice versa. The light source can be either a laser or a wide spectrum source such as a xenon lamp. In the latter case a scanning monochromator is inserted after the light source or before the detector, which enables spectroscopic measurements.

Ellipsometers may be of a rotating element type in which an optical element is continuously rotated. The rotation results in a harmonic output signal from the detector, from which the ellipsometric parameters $\psi$ and $\Delta$ may be determined. This setup is fast and quite accurate: measurable changes may be 0.03° for $\psi$ and 0.2° for $\Delta$.

Rotating element ellipsometers are versatile research instruments, but not well suited for imaging purposes. A nulling ellipsometer is historically an older setup and may be better suited for imaging. In the nulling ellipsometer, the orientation of the analyzer, the polarizer, or the retarder is set to a fixed value. The two remaining elements are then rotated such that the intensity on the detector is zero. This process is called "nulling". From the polarizer, compensator and analyzer settings the ellipsometric parameters can be calculated. The main advantage of the nulling ellipsometer may be its sensitivity and a drawback may be that finding the null condition takes time. When the properties of a surface change, the null condition is not met anymore, and intensity may be detected. By adjusting the component settings such that the null condition is restored, the ellipsometric parameters of the surface can be tracked as a function of time and/or position on the sample. In this way, null ellipsometry can be used as a sensor, or as an imaging system. By nulling on a clean part of a surface, a contaminated part will show up as a bright spot.

To improve the measurement speed, the components can be fixed at values that are derived from an initial null condition. In this situation, changes in the surface properties or scanning of the surface results in a change of the measured intensity:

$$\delta I = R_s \left(\frac{\tan\psi}{1 + \tan\psi}\right)^2 \left\{\left(\frac{\delta(\tan\psi)}{\tan\psi}\right)^2 + \delta\Delta^2\right\} \quad (4)$$

In this equation, $R_S$ is the intensity reflection coefficient for perpendicular polarized light, $\delta(\tan\psi)$ and $\delta\Delta$ are the changes in the ellipsometric parameters and $\delta I$ is the intensity transmitted by the system, normalized with the intensity of the source.

A number of experiments have been conducted to investigate detection of small particles on flat surfaces and to answer the question whether particles can be detected on samples with a periodic structure. PSL particles are used since they may form a worst case scenario due to their low refractive index.

The imaging ellipsometer used for the experiments was a PCSA (polarizer, compensator, sample, and analyzer) spectroscopic imaging ellipsometer. The radiation system of this ellipsometer is comprised of a laser, a polarizer and a compensator. On the imaging side, the setup is comprised of a standard microscopic objective with a long working distance, an analyzer and a CCD camera. The contrast is created by adjusting the polarizer and analyzer such that light reflected on the background of the sample (i.e. the clean surface) is completely or nearly completely blocked. Particles or defects on the surface are then imaged as small spots with an intensity that deviates from the background. The resolution of the system is determined by the applied wavelength and the microscope objective.

Since the ellipsometer records an image at an adjustable angle the plane of focus intersects with the surface at a focal line. To create a sharp image of the entire field of view, the focal line is scanned over the surface by changing the objective distance. This process takes a few seconds.

To obtain the ellipsometric angles $\psi$ and $\Delta$, several images are measured at different polarizer and analyzer settings. For every pixel in the image component, settings that yield zero intensity are determined, and from these values $\psi$ and $\Delta$ are calculated. The images shown in the Figures are measured at a reflection angle of 58 degrees.

Figure 2A:
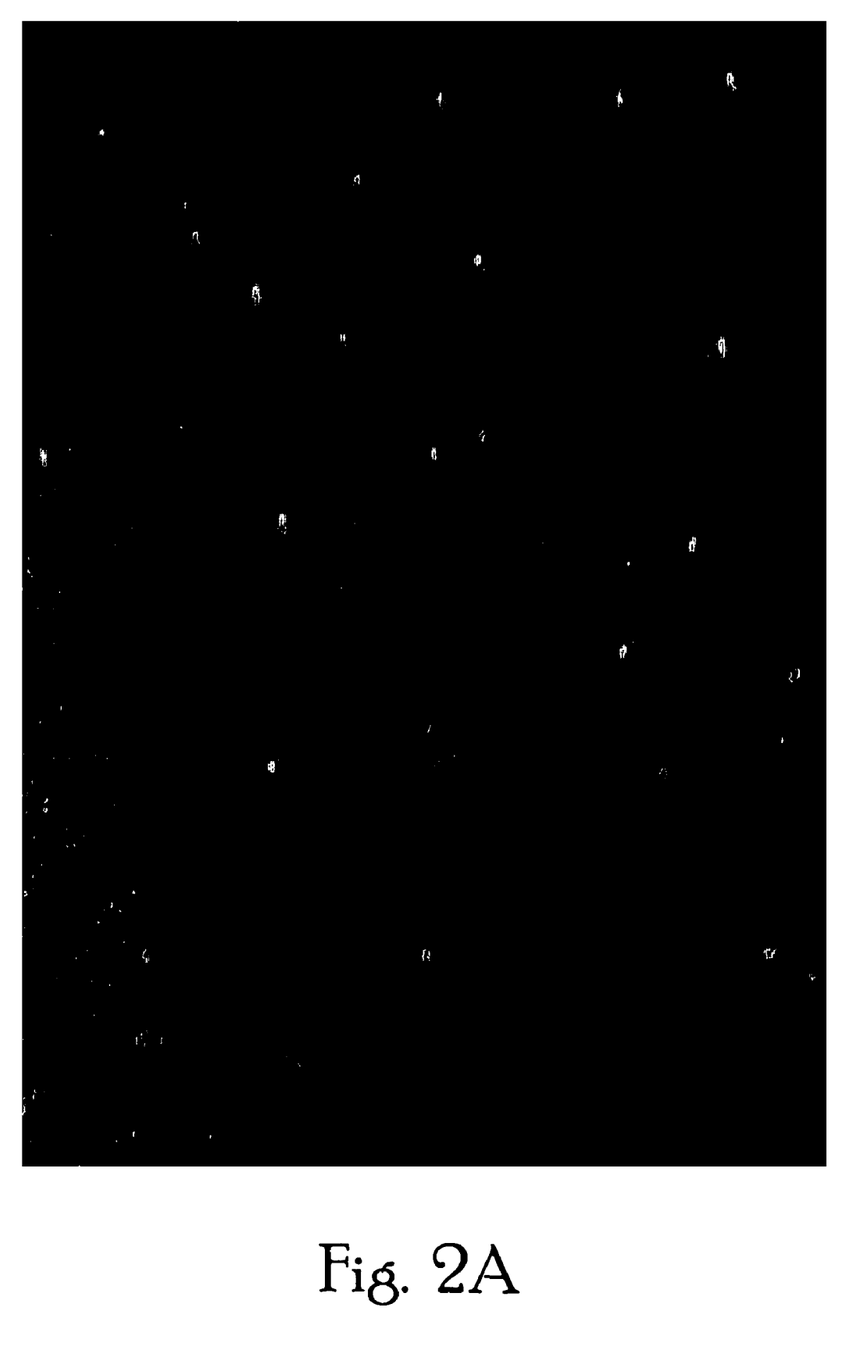
FIGS. 2A-B show two ellipsometry images of anomalies (i.e. 60 nm particles) on a sample (i.e. a silicon wafer)
Figure 2B:
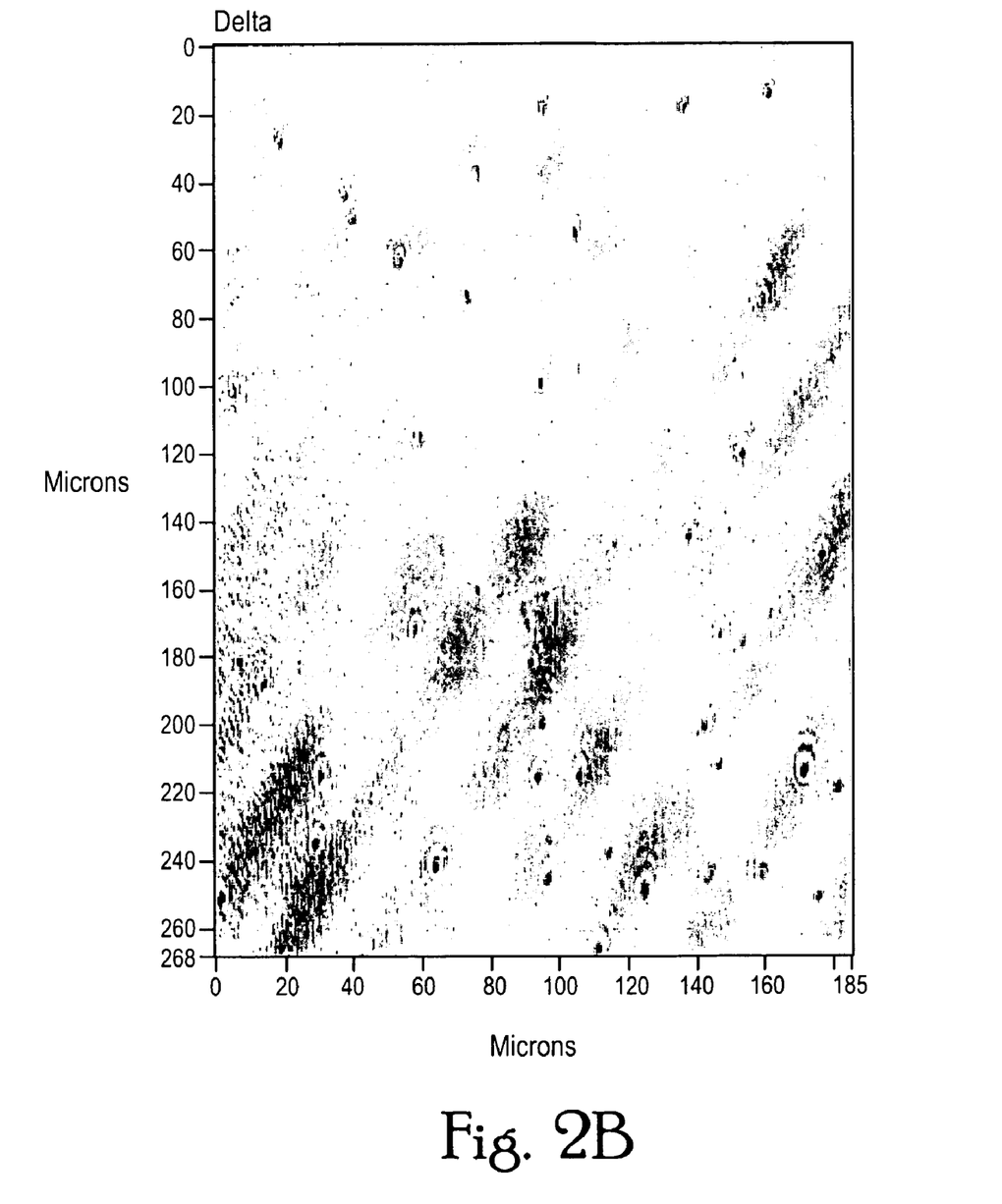

FIGS. 2A-B show ellipsometry images of a silicon wafer with $1.3 \cdot 10^3$ 60 nm PSL particles per square millimeter. FIG. 2A is an intensity image measured with fixed polarizer and analyzer settings, and by nulling the background and maximizing both the laser power and the camera gain. This maximizes the sensitivity of the setup and the particles are clearly visible. Note that the intensity of the background is not completely zero; the measurement is carried out slightly out of the null condition, where the sensitivity is improved.

FIG. 2B shows a map of Δ with a range of 1.7°, Δ being the phase difference between the reflection coefficient for p- and s-polarized light. The particles are more visible than in the intensity image, but due to the high sensitivity, a regular disturbance may also be seen. This disturbance is probably caused by instrument imperfections. Because of the regular structure and the relatively large period, the regular disturbance may be removed, if necessary, using digital image processing.

The number of observed particles per square millimeter is $7.7 \cdot 10^2$, which is similar to the number measured previously. The factor 1.7 difference is easily accounted for by the inhomogeneity of the particle coverage. Although background scattering may be a problem, it is not as fundamental as it is in scattering based particle scanners. Because ellipsometry is based on measurements of the specular reflected beam, stray light can be suppressed by eliminating as much of the scattered light as possible. This may be achieved by optimizing the experimental settings of the ellipsometer. The imaging ellipsometer has three degrees of freedom: the angles of the polarizer, the compensator and the analyzer. Two of these degrees of freedom are used to fulfill the null intensity condition. The third degree of freedom and possibly the angle of detection to the normal of the surface of the patterning device and the wavelength of the radiation can be varied to optimize the detection of particles on a particular structured background.

Figure 3A:
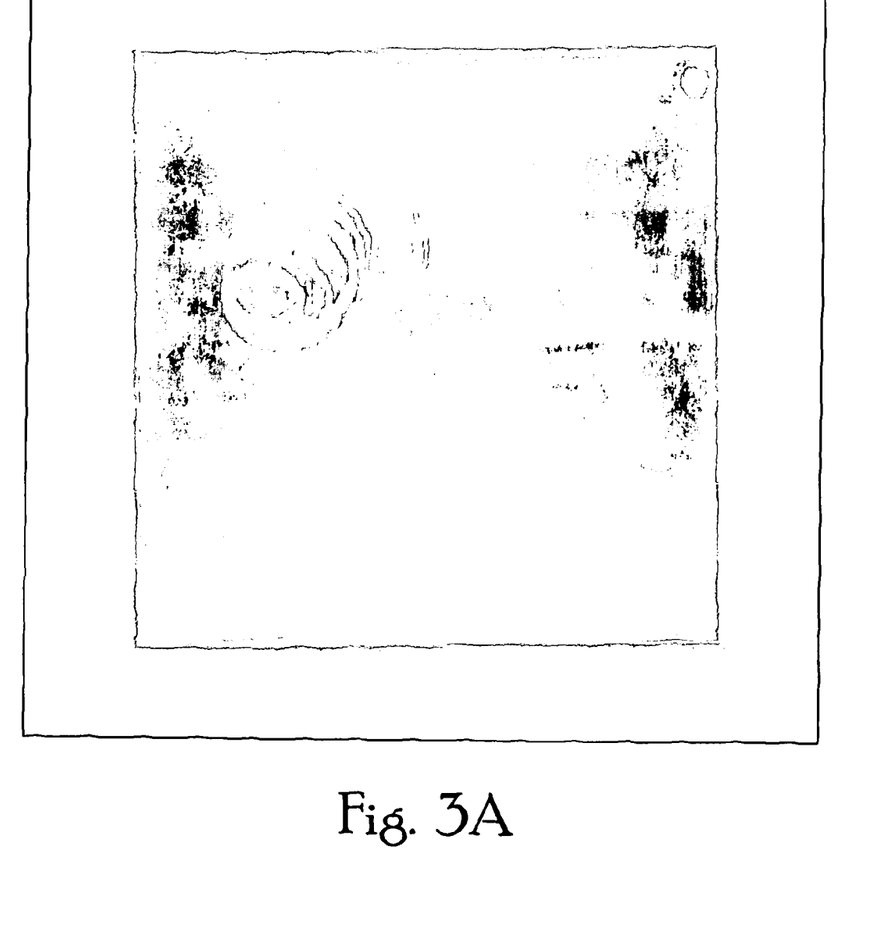
FIGS. 3A-C depict three images of a sample comprising two different structures with a minimum feature size of 250 nm that have been nulled with different polarizer and retarder settings.
Figure 3B:
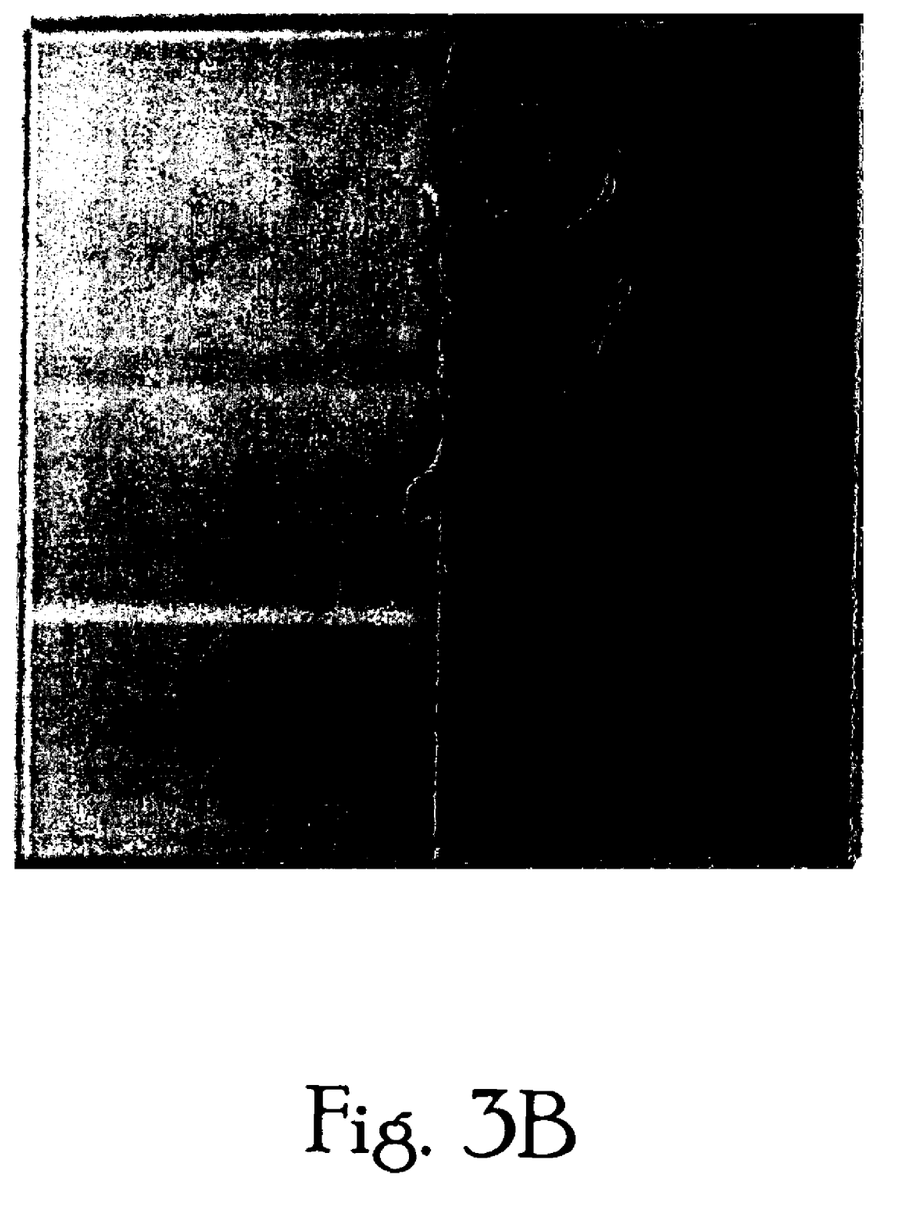
Figure 3C:
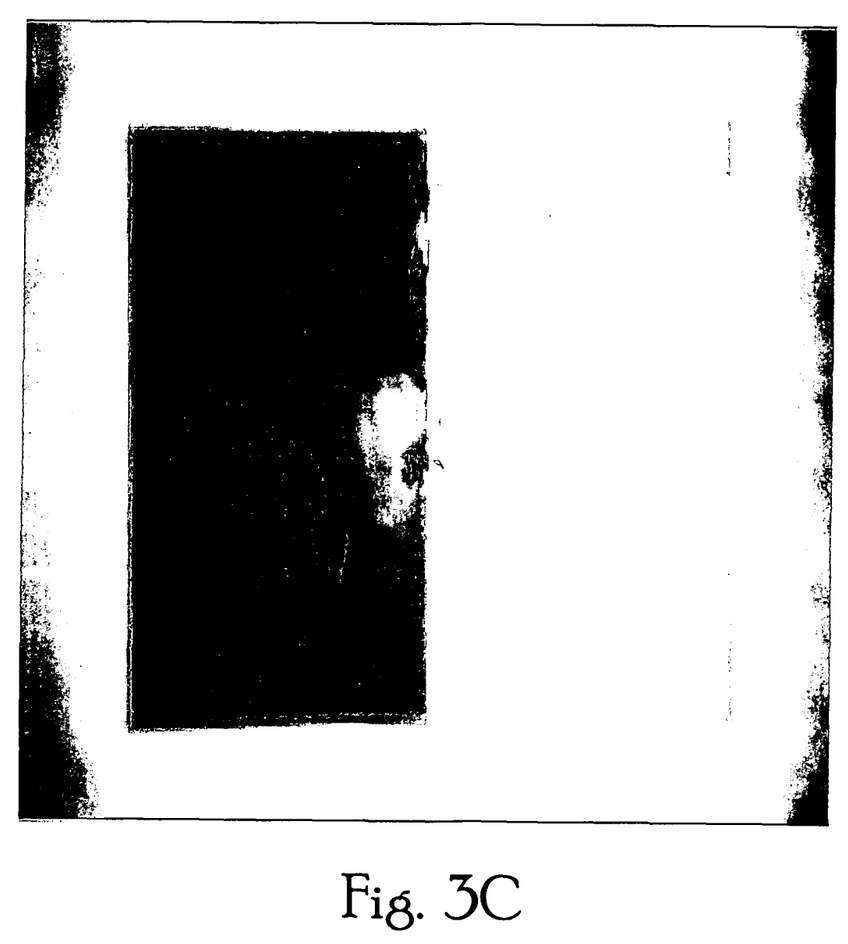

Having the capability to null the reflection from the structure allows for the applicability of ellipsometry for particle detection on structured surfaces. FIGS. 3A-C show two different structures. The top side shows a 1 square millimeter area with two different structured areas that have a minimum feature size of 250 nm. Three images have been measured with different polarizer and analyzer settings. Imaging has been done with a low magnification using a 2× objective, so the structures are not resolved. The images show that the reflection of both the left and the right structure can be nulled, which should be a prerequisite for detection of particles or other defects. Note that the reflection from the background is very strong due to its different optical properties.

Two possibilities exist to avoid resolution of a structure. First, measurements can be done at a lower magnification as in the upper images of FIG. 3. This has the obvious disadvantage that detection of particles or defects will get equally harder. The other option is to measure at longer wavelengths, which will also "blur" a regular structure to a homogeneous background. This will not significantly affect the strength of the ellipsometer signal.

Figure 4:
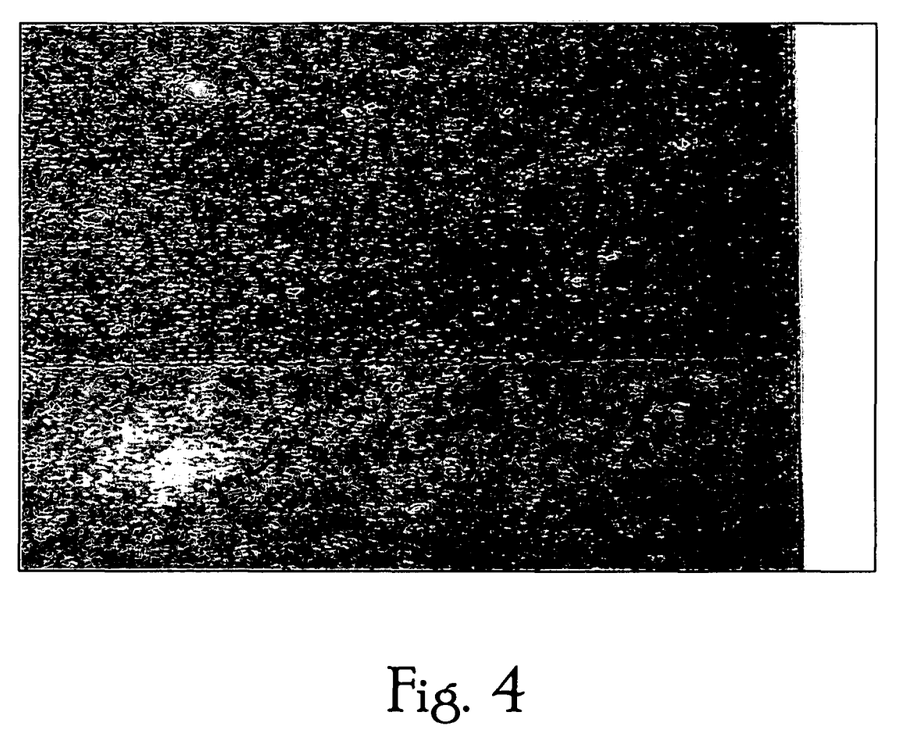
FIG. 4 shows an image of a sample with two different structures, recorded with a 10× objective.

FIG. 4 shows an image of the area with two different structures, recorded with a 10× objective. In the middle, a separation between two different areas is visible, with the upper area nearly nulled. On the right, the flat background is visible as a high intensity area. Dust particles are clearly visible at several places. Although this is only a crude experiment, it shows that individual particles can be detected on surfaces with a regular structure, even if the structure is not optically resolved.

Although specific reference may be made in this text to the use or lithographic systems in the manufacture of ICs, it should be understood that the lithographic system described herein may have other applications, such as the manufacture of integrated optical systems, guidance and detection patterns for magnetic domain memories, flat-panel displays, liquid-crystal displays (LCDs), thin-film magnetic heads, etc.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured. It may be necessary to inspect the imprint mask for contaminant particles with an inspection apparatus according to the invention.

Furthermore, although the illustrated embodiments suggest an orientation of the object with the patterned surface oriented opposite to the direction of gravity, the position of the object is not limited thereto and may be oriented otherwise, in particular, in an orientation wherein the patterned surface is scanned with the surface oriented along the direction of gravity. This may have as a benefit that it will minimize the risk of collecting particles during the scan process.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

What is claimed is:

1. An inspection apparatus for inspecting a sample for anomalies, wherein the apparatus is a nulling imaging ellipsometer, the apparatus comprising:
    a support structure configured and arranged to support the sample;
    a radiation system configured and arranged to radiate the sample with a polarized radiation beam, the radiation system being provided with a first polarizer;
    an adjustable retarder; and
    a detection system including
        an adjustable second polarizer; and
        a detector,
        wherein the adjustable second polarizer and the adjustable retarder are configured to null a portion of a reflected radiation beam that is reflected from a clean portion of the sample,
        wherein the detection system is configured and arranged to detect, with the detector, the reflected radiation beam; and,
    a control system configured and arranged to control a rotation of the first polarizer, the second polarizer, the retarder, or any combination thereof such that, for an image component corresponding to the sample, settings that yield zero intensity on the detector are determined, so as to yield the ellipsometric angles $\psi$ and $\Delta$ as functions of time and position on the sample.

2. The apparatus according to claim 1, wherein the detector is a camera.

3. The apparatus according to claim 1, wherein a magnifying optical projection system is provided to the detection system.

4. The apparatus according to claim 3, wherein the magnifying optical projection system has a magnification between 10 to 100 times.

5. The apparatus according to claim 1, wherein the sample is a patterning device.

6. The apparatus according to claim 1, wherein the anomalies are particles.

7. The apparatus according to claim 6, wherein the particles are smaller than about 200 nm.

8. The apparatus according to claim 1, wherein the radiation system is configured and arranged to radiate light with a wavelength in between 150 and 2000 nm.

9. The apparatus according to claim 8, wherein the radiation system is configured and arranged to radiate light with a wavelength that is larger than the size of a patterned structure on the sample.

10. The apparatus according to claim 1, wherein the apparatus is configured and arranged to scan the support structure with respect to the radiation system and the detection system while scanning the sample for anomalies.

11. The apparatus according to claim 1, wherein the apparatus is provided with a rotating support structure configured and arranged to rotate the sample with respect to the radiation system and detection system for inspecting both sides of the sample.

12. The apparatus according to claim 1, wherein the retarder is a quarter wave plate and is rotatable by a rotator.

13. The apparatus according to claim 1, wherein the retarder is provided to the radiation system.

14. The apparatus according to claim 1, wherein the retarder is provided to the detection system.

15. The apparatus according to claim 1, wherein the apparatus is provided with a modulation system configured and arranged to provide a small modulation to the radiation beam or the reflected radiation beam.

16. The apparatus according to claim 1, wherein the apparatus is configured and arranged to radiate the radiation beam to the sample at an angle with respect to a normal of the sample, and to detect the at the same angle from the normal, the angle being larger than zero degrees.

17. The apparatus according to claim 1, wherein the anomalies comprise defects in a pattern provided to the sample.

18. A lithographic system comprising:
a patterning device support configured and arranged to support a patterning device, the patterning device being capable of imparting a radiation beam with a pattern in its cross-section to form a patterned radiation beam;
a substrate table configured and arranged to hold a substrate;
a projection system configured and arranged to project the patterned radiation beam onto a target portion of the substrate; and
an inspection apparatus configured and arranged to inspect the patterning device, wherein the apparatus is a nulling imaging ellipsometer, the inspection apparatus comprising:
a radiation system configured and arranged to radiate the patterning device with a second radiation beam that is polarized, the radiation system being provided with a first polarizer;
an adjustable retarder; and
a detection system including
an adjustable second polarizer; and
a detector,
a control system configured and arranged to control a rotation of the first polarizer, the second polarizer, the retarder, or any combination thereof such that, for an image component corresponding to the patterning device, settings that yield zero intensity on the detector, are determined, so as to yield the ellipsometric angles $\psi$ and $\Delta$ as functions of time and position on the patterning device.

19. The lithographic system according to claim 18, further comprising a vacuum space configured and arranged to contain the patterning device, wherein the inspection apparatus is provided outside of the vacuum space.

20. A method for inspecting a sample for anomalies, using an inspection apparatus having a detector and configured to adjust a radiation beam with a first polarizer, a second polarizer, a retarder, and a radiation system, wherein the apparatus is a nulling imaging ellipsometer comprising:
polarizing the radiation beam with the first polarizer;
directing the radiation beam to the sample with the radiation system;
using a control system configured and arranged to control a rotation of the first polarizer, the second polarizer, the retarder, or any combination thereof such that, for an image component corresponding to the sample, settings that yield zero intensity on the detector are determined, so as to yield the ellipsometric angles $\psi$ and $\Delta$ as functions of time and position on the sample; and,
using the determined values of the ellipsometric angles $\psi$ and $\Delta$ to inspect a sample and detect anomalies.

21. The method according to claim 20, further comprising rotating the retarder and the first polarizer such that the sample produces a linearly polarized radiation beam.

22. The method according to claim 21, further comprising rotating the second polarizer until the linearly polarized radiation beam shows no substantial intensity on the detector when a clean sample is inspected.

23. The method according to claim 20, further comprising rotating the first polarizer and the retarder such that the retarder produces a linearly polarized radiation beam.

24. The method according to claim 23, further comprising rotating the second polarizer until the linearly polarized radiation beam shows no substantial intensity on the detector when a clean sample is inspected.

25. The method according to claim 20, wherein a signal on the detector indicates an anomaly on the sample.

26. The method according to claim 20, wherein a signal on the detector indicates a structural defect on the sample.

27. The method according to claim 20, wherein the sample is a patterning device.

28. The method according to claim 20, further comprising continuously rotating the first and second polarizers.

29. A method for inspecting a clamping surface of a support structure, using an inspection apparatus having a detector and a control system configured to adjust a radiation beam with a first polarizer, and a second polarizer, wherein the apparatus is a nulling imaging ellipsometer comprising:
polarizing the radiation beam with the first polarizer;
directing the radiation beam to the clamping surface of the support structure;
receiving the reflected detection beam from the clamping surface of the support structure, via the second polarizer, with the detector; and using the control system configured and arranged to control a rotation of the first polarizer, the second polarizer, the retarder, or any combination thereof such that, for an image component corresponding to the clamping surface, settings that yield zero intensity on the detector are determined, so as to yield the ellipsometric angles $\psi$ and $\Delta$ as functions of time and position on the clamping surface; and using the determined values of the ellipsometric angles $\psi$ and $\Delta$ to inspect a clamping surface for anomalies.

30. The method according to claim 29, wherein the inspection apparatus has a retarder, further comprising:

adjusting at least one of the first polarizer, second polarizer, and the retarder so that the radiation reflected from the clamping surface is nulled.

31. The method according to claim 29, further comprising continuously rotating the first and second polarizers.

* * * * *